(12) United States Patent
Benz et al.

(10) Patent No.: US 10,539,574 B2
(45) Date of Patent: Jan. 21, 2020

(54) IDENTITY AND PURITY OF TISSUE BIOPSIES

(71) Applicant: TETEC Tissue Engineering Technologies AG, Reutlingen (DE)

(72) Inventors: Karin Benz, Göppingen (DE); Christian Freudigmann, Reutlingen (DE); Christoph Gaissmaier, Kusterdingen (DE); Jochen Hecky, Freiburg (DE); Jürgen Mollenhauer, Reutlingen (DE)

(73) Assignee: TETEC Tissue Engineening Technologies AG, Reutlingen (DE)

( * ) Notice: Subject to any disclaimer, the term of this patent is extended or adjusted under 35 U.S.C. 154(b) by 63 days.

(21) Appl. No.: 15/324,076

(22) PCT Filed: Jul. 10, 2015

(86) PCT No.: PCT/EP2015/065782
§ 371 (c)(1),
(2) Date: Jan. 5, 2017

(87) PCT Pub. No.: WO2016/005543
PCT Pub. Date: Jan. 14, 2016

(65) Prior Publication Data
US 2017/0261515 A1    Sep. 14, 2017

(30) Foreign Application Priority Data
Jul. 11, 2014    (DE) .................. 10 2014 213 571

(51) Int. Cl.
*G01N 33/68*    (2006.01)
*C12N 5/077*    (2010.01)
*G01N 33/53*    (2006.01)

(52) U.S. Cl.
CPC ....... *G01N 33/6887* (2013.01); *C12N 5/0655* (2013.01); *C12Y 304/24007* (2013.01); *G01N 2333/78* (2013.01)

(58) Field of Classification Search
None
See application file for complete search history.

(56) References Cited

U.S. PATENT DOCUMENTS

| | | |
|---|---|---|
| 5,541,295 A | 7/1996 | Barrach et al. |
| 6,132,975 A | 10/2000 | Kanan et al. |
| 6,132,976 A | 10/2000 | Poole et al. |
| 2004/0214349 A1* | 10/2004 | Bateman ................ A61K 38/36 436/520 |
| 2011/0151489 A1* | 6/2011 | Amir .................. G01N 33/6881 435/7.92 |

OTHER PUBLICATIONS

Brady et al. (Clinical Science 1999 vol. 96, p. 209-215) (Year: 1999).*
Erat et al. (PNAS 2009, vol. 106, p. 4195-4200) (Year: 2009).*
Tabassi et al. (Osteoarthritis and Cartilage 2008 vol. 16, p. 1183-1191) (Year: 2010).*
Eyre et al. (J. Biol. Chem. 2010 page total 18 pages) (Year: 2010).*
Olsen, A.K. Anabolic and catabolic function of chondrocyte ex vivo is reflected by the metabolic processing on type II collagen. Osteoarthritis and Cartilage (2007) 15:335-342.
Charni-Ben Tabassi, N. The type II collagen fragments Helix-II and CTX-II reveal different enzymatic pathways of human cartilage collagen deg. radiation. Osteoarthritis (2008) 16:1183-1191.
Dickinson, S.C., et al. Quantitative outcome measures of cartilage repair in patients treated with tissue engineering, Tissue Engineering, Larchmont, NY, US vol. 11, No. 1-2, Jan. 1, 2005, abstract, material and methods, p. 280, col. 2, last paragraph—p. 285 first paragraph, figures 2, 4-5.
Hollander, A.P., et al. Quantitative analysis of repair tissue biopsies following chondrocyte implantation. Discussion, Novartis Foundation Symposium, Wiley, Chichester, GB, vol. 249, Jan. 1, 2003, p. 218-241, abstract p. 219 last paragraph—p. 220, material and methods, p. 222 last paragraph—p. 224.
Kelly, D.J., et al. Biochemical markers of the mechanical quality of engineered hyaline cartilage. Journal of Materials Science: materials in medicine, Kluwer Academic Publishers, BO, vol. 18, No. 2, Feb. 1, 2007, p. 273-281.
Mollenhauer J, Kuettner K.E. Articular Cartilage in Principles of Orthopaedic Practice. 2nd Edition. Eds: R. Dee, L.C. Hurst, M.A. Gruber, S.A. Kottneier. New York, McGraw Hill, 1997.
Poole, A.R. Immunochemical markers of joint inflammation, skeleton damage and repair: where are we now? Ann Rheum Dis. (Jan. 1994) 53(1):3-5.
Gamero P, Pipemo M, Gineyts E, Christgau S, Delmas PD, Vignon E. Cross sectional evaluation of biochemical markers of bone, cartilage, and synovial tissue metabolism in patients with knee osteoarthritis: relations with disease activity and joint damage. Ann Rheum Dis. (Jun. 2001) 60(6):619-626.
Herrmann M, Seibel MJ. The amino- and carboxyterminal cross-linked telopeptides of collagen type I, NTX-I and XTX-I. (a comparative review). Clin Chim Acta. Jul. 17, 2008 292(2):57-75.
Gamero et al. Association of Baseline Levels of Marker of Bone and Cartilage Degradation are associated with Longterm Progression of Joint Damage in Patients with Early Rheumatoid Arthritis: The Cobra Study. Arthritis Rheum. (2002a) 46(11):2847-57.

(Continued)

*Primary Examiner* — Changhwa J Cheu
(74) *Attorney, Agent, or Firm* — Lewis Kohn & Walker LLP; David M. Kohn (57) ABSTRACT

A method for the in vitro detection of cartilage tissue and/or for the in vitro determination of the purity of cartilage tissue includes: a) treating a tissue sample with a protease and b) testing the protease-treated tissue sample for the presence of protease-resistant fragments of type II collagen and/or type I collagen. Methods can be carried out for preparing a cartilage cell culture, and for preparing a cartilage cell-loaded implant. Protease-resistant fragments of type II collagen and/or type I collagen can be used for the in vitro detection of cartilage tissue and/or for the in vitro determination of the purity of cartilage tissue. A kit can be used for carrying out the methods.

10 Claims, 9 Drawing Sheets
Specification includes a Sequence Listing.

(56) References Cited

OTHER PUBLICATIONS

Gamero et al. Uncoupling of type II collagen synthesis and degradation predicts progression of joint damage in patients with knee osteoarthritis. Arthritis Rheum. (2002b) 46(10):2613-24.
Christgau et al. Collagen type II C-telopeptide fragments as an Index of Cartilage degradation. Bone (2001) 29:209-215 doi: 10.1016/j.cca.2008.03.020 Epub Mar. 27, 2008 and Review. Erratum in Clin Chim Acta. Nov. 2008, 397(1-2):103.
Kohler, Milstein: Continuous cultures of fused cells secreting antibody of predefined specificity. Nature (1975) 256(5517):495-7.
Campbell, A.M. Laboratory Techniques in Biochemistry and Molecular Biology, vol. 13 (1986).

* cited by examiner

SEQUENCE LISTING

```
<160> NUMBER OF SEQ ID NOS: 2

<210> SEQ ID NO 1
<211> LENGTH: 6
<212> TYPE: PRT
<213> ORGANISM: Artificial Sequence
<220> FEATURE:
<223> OTHER INFORMATION: CTX-II

<400> SEQUENCE: 1

Glu Lys Gly Pro Asp Pro
1               5

<210> SEQ ID NO 2
<211> LENGTH: 10
<212> TYPE: PRT
<213> ORGANISM: Artificial Sequence
<220> FEATURE:
<223> OTHER INFORMATION: CTX-II

<400> SEQUENCE: 2

Thr Gly Val Glu Gly Pro Lys Gly Asp Thr
1               5                   10
```

IDENTITY AND PURITY OF TISSUE BIOPSIES

RELATED APPLICATION(S)

This application is the United States national phase entry of International Application No. PCT/EP2015/065782, filed Jul. 10, 2015, which is related to and claims the benefit of priority of German Application No. DE 10 2014 213 571.0, filed Jul. 11, 2014. The contents of International Application No. PCT/EP2015/065782 and German Application No. DE 10 2014 213 571.0 are incorporated by reference herein in their entireties.

FIELD

The invention relates to a method for the in vitro detection and/or for the in vitro determination of the purity of cartilage tissue, to a method for preparing a cartilage cell culture, to a method for preparing a cartilage cell-loaded implant, to the use of protease-resistant fragments of type II collagen and/or type I collagen and also to the use of a kit.

BACKGROUND

In order to carry out a matrix-assisted chondrocyte transplantation (MACT), it is necessary to be able to provide quantitative information concerning the identity and purity of the cartilage tissue used and of the cartilage cells (chondrocytes) used that are to enter the implants or matrices intended for implantation.

Up to now, the identity of the cartilage tissue used has been detected via the site of removal. However, this anatomical procedure lacks documentation verifying correct removal and does not allow a quantification of the removed tissue material with regard to purity in relation to bone and connective tissue.

In the case of a piece of cartilage tissue removed from a human or animal knee joint, it is, for example, not possible to rule out a contamination with connective tissue, such as synovia for example, and/or subchondral bone. Moreover, the identity of the cartilage tissue is open to question in cases in which the nature of the biopsy does not allow an unambiguous anatomical assignment.

In principle, the identity and the purity of cartilage biopsies can be examined immunohistologically. Besides problems of practical implementation under cleanroom conditions, immunohistological examinations have, however, the disadvantage that invariably only small segments of the prepared cartilage are assessable, since histological sections typically have a thickness of <10 µm. A comprehensive detection of identity and purity that includes the entire preparation is therefore not possible.

SUMMARY

It is therefore an object of the present invention to provide a method for the in vitro detection and/or for the in vitro determination of the purity of cartilage tissue, which method avoids disadvantages known from the prior art. It is intended that the method allow in particular an unequivocal determination of identity and, at the same time, a determination of purity of cartilage tissue. It is a further object of the invention to provide a method for preparing a cartilage cell culture and a method for preparing a cartilage cell-loaded implant. Moreover, it is an object of the invention to provide for the use of protease-resistant collagen fragments and for the use of a kit for carrying out the aforementioned methods.

These objects are achieved by methods as described herein.

In a first aspect, the invention provides a method for the in vitro detection, i.e., for the in vitro identification, of cartilage tissue and/or for the in vitro determination of the purity of cartilage tissue. The cartilage tissue is preferably hyaline, more particularly articular, cartilage tissue. The method comprises the following steps:
a) treating a tissue sample with a protease and
b) testing the protease-treated tissue sample for the presence of protease-resistant fragments of type II collagen and/or of protease-resistant fragments of type I collagen.

In other words, when step b) is carried out, the protease-treated, i.e., protease-digested, tissue sample is tested for collagen fragments which are protease-resistant, i.e., stable with respect to a protease, and which arise or are released as a result of degradation of type II collagen and/or as a result of degradation of type I collagen.

When step a) is carried out, the tissue sample is generally liquefied, and so the above-mentioned collagen fragments are generally released into a liquefied tissue sample.

Type II collagen generally represents the dominant collagen for cartilage tissue. This collagen type is not found in connective tissue, such as synovia for example, or bone tissue, such as subchondral bone tissue for example. Both connective tissue and bone tissue may, for example, occur in joint biopsies as contaminating foreign tissue. Connective tissue and bone tissue both contain type I collagen as dominant collagen, which in turn does not occur in cartilage tissue.

The invention is, then, based on the surprising finding that protease-resistant fragments of type II collagen and/or type I collagen allow the determination of the identity and of the purity of cartilage tissue. In this connection, it was possible to establish in particular that the amount of released protease-resistant fragments of type II collagen is proportional to the amount of cartilage present in the sample and the amount of released protease-resistant fragments of type I collagen is proportional to the amount of foreign tissue present in the sample. This in turn allows not only a mere identification of cartilage tissue, but also, in the case of the presence of foreign tissue, a quantifying identification of cartilage tissue, i.e., a determination of the degree of purity of cartilage tissue detected or identified in the sample.

If, in the context of the method according to the invention, it is established that the tissue sample tested according to step b) contains protease-resistant fragments of type II collagen, the sample can be assigned to cartilage tissue. If, at the same time, it is established that the tissue sample does not contain protease-resistant fragments of type I collagen, the tested sample is pure cartilage tissue. In other words, pure cartilage tissue is identified by the detection of protease-resistant fragments of type II collagen with simultaneous absence of protease-resistant fragments of type I collagen. Since cartilage tissue consists of only one cell type, namely the so-called chondrocytes (cartilage cells) (Mollenhauer J, Kuettner K E: Articular Cartilage. In: Principles of Orthopaedic Practice. 2nd edition. Eds: R. Dee, L. C. Hurst, M. A. Gruber, Stephen A. Kottmeier. New York, McGraw Hill, 1997), the method according to the invention additionally allows an unambiguous identification of chondrocytes via a successful identification of cartilage tissue.

If, in the context of the method according to the invention, it is established that the tissue sample tested according to step b) contains not only protease-resistant fragments of type II collagen but also protease-resistant fragments of type I collagen, the sample can be assigned to cartilage tissue contaminated with foreign cells and/or foreign tissue. Moreover, via the released amounts of protease-resistant fragments of type II collagen and type I collagen, it is possible to determine the degree of purity of the sample with regard to cartilage tissue. Possible foreign cells are mainly fibroblasts, endothelial cells and/or osteoblasts. Possible foreign tissues are the already mentioned connective tissue and bone tissue.

Lastly, if, in the context of the method according to the invention, it is established that the tissue sample tested according to step b) does not contain protease-resistant fragments of type II collagen, the presence of cartilage tissue can be ruled out.

A particular advantage that should be highlighted is that the method according to the invention allows a specific identification of tissue samples which, owing to their degree of purity with regard to cartilage tissue, are especially suitable as starting material for a successful cartilage cell culture and, in particular, for a successful cartilage cell implantation, preferably matrix-assisted chondrocyte transplantation (MACT).

In a preferred embodiment, the method according to the invention is intended for the in vitro detection of cartilage tissue and for the in vitro determination of the purity of cartilage tissue.

Preferably, when step b) is carried out, the protease-treated tissue sample is tested both for protease-resistant fragments of type II collagen and for protease-resistant fragments of type I collagen.

In a further embodiment, the tissue sample is a human or animal, preferably human, tissue biopsy or a fragment of such a tissue biopsy.

In a further embodiment, the tissue sample is a cartilage biopsy or a fragment thereof. In the context of the present invention, the expression "cartilage biopsy" is intended to comprehend not only biopsies consisting exclusively of cartilage tissue, i.e., of pure cartilage tissue, but also biopsies containing in addition to cartilage tissue other tissue types, more particularly connective tissue, such as synovia for example, and/or bone tissue, such as subchondral bone tissue for example, and/or in addition to cartilage cells other cell types, such as fibroblasts, endothelial cells and/or osteoblasts for example.

In a further embodiment, the tissue sample is a joint biopsy, more particularly knee joint biopsy, or a fragment thereof.

In a further embodiment, the tissue sample is cleaned mechanically, more particularly with the aid of a scalpel, before step a) is carried out.

In a further embodiment, connective tissue (such as synovia for example), superficial cartilage tissue, mineralized cartilage tissue and/or bone tissue, more particularly subchondral bone tissue, are removed from the tissue sample before step a) is carried out. Such a cleaning operation may be advantageous when the tissue sample is provided from a so-called cartilage/bone core biopsy, especially as described in the paragraph which follows.

Figure 1:
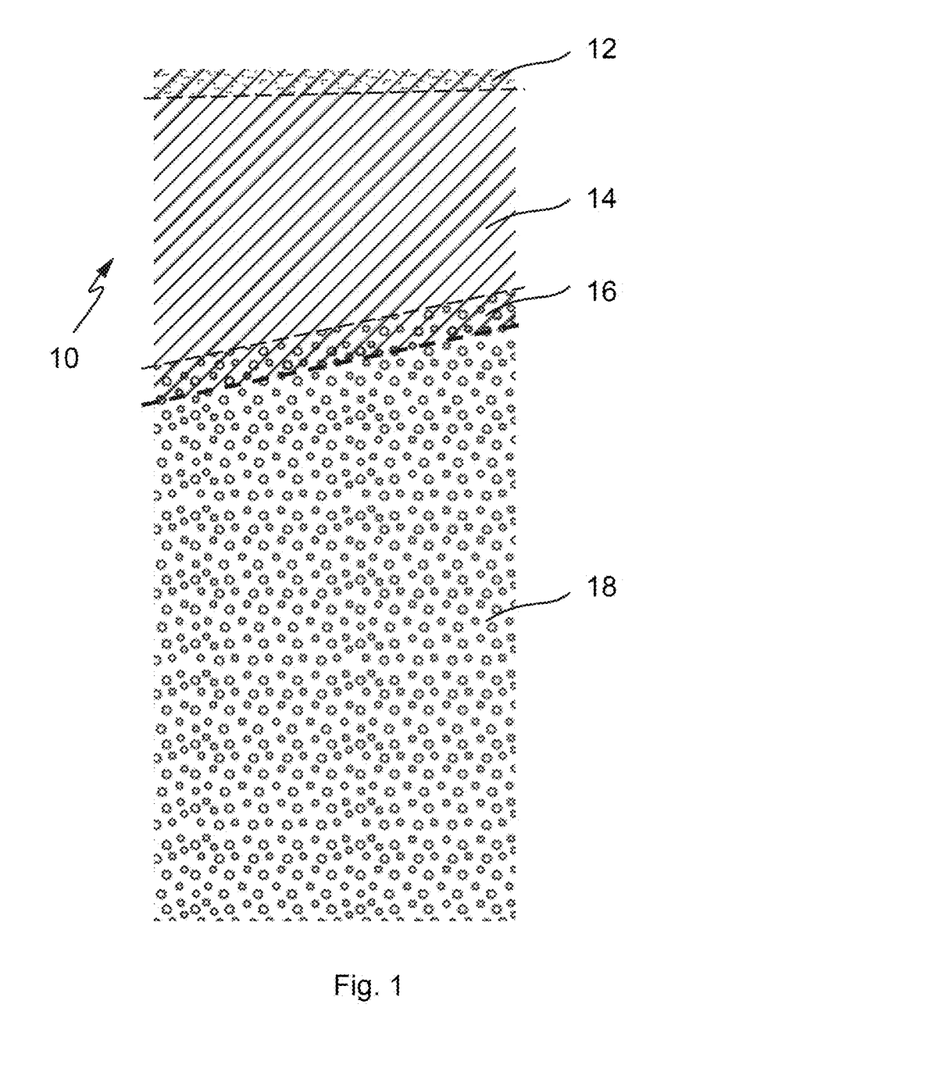
FIG. 1 shows schematically the anatomical structure of a bone/cartilage core 10 removed from a knee joint of a human patient. Layer 12 is the so-called superficial cartilage layer. The underlying middle cartilage layer 14 is intended for the actual provision of the cartilage tissue and of the cartilage cells. Situated therebelow is a mineralized cartilage layer 16, followed by an underlying subchondral bone layer 18. Since bone and mineralized cartilage generally cannot be cut through, a separation takes place along the dashed line, i.e., at the base of the nonmineralized cartilage layer 14. The dotted line indicates the course of the cartilage/bone boundary.

In a further embodiment, the tissue biopsy is a tissue fragment, more particularly a cartilage tissue fragment, of a cartilage/bone core biopsy. The core biopsy is generally removed in the form of a cylinder and preferably from a human or animal knee joint. Such a core biopsy has a typical anatomical structure comprising a superficial cartilage layer, an underlying middle cartilage layer, a mineralized cartilage layer lying below the middle cartilage layer, and a subchondral bone layer lying below the mineralized cartilage layer (see also FIG. 1). Preferably, the tissue fragment comes from the middle cartilage layer of the cartilage/bone core biopsy.

In a further embodiment, the tissue sample is treated with the protease over a period of from 12 h to h, more particularly from 14 h to 24 h, preferably from 19 h to 24 h.

In a further embodiment, the protease is collagenase, preferably bacterial collagenase. A suitable protease is, for example, commercially available under the name Liberase (Roche).

In an advantageous embodiment, a solution (so-called digest solution) is obtained when step a) is carried out. The advantage of this is that a homogeneous distribution of the protease-resistant fragments of type II collagen and/or type I collagen is possible, whereby an aliquot of such a solution represents a representative cross section of the tissue sample to be tested. This makes a comprehensive detection of identity and purity possible, in contrast to immunohistological examinations.

In a further embodiment, the protease-resistant fragments of type II collagen and/or type I collagen are crosslinked collagen fragments. In other words, the protease-resistant fragments of type II collagen and/or type I collagen can have crosslinks. The crosslinks can optionally be free of peptide bonds.

More particularly, the crosslinks can be selected from the group comprising allysine crosslinks, hydroxyallysine crosslinks, dehydrohydroxylysinonorleucine crosslinks, dehydrolysinonorleucine crosslinks, hydroxylysino-5-ketonorleucine crosslinks, dihydroxylysinonorleucine crosslinks, histidinohydroxylysinonorleucine crosslinks, hydroxylysylpyridinoline crosslinks, lysylpyridinoline crosslinks, pyridinium crosslinks, 3-hydroxypyridinium crosslinks, histidinohydroxymerodesmosine crosslinks and combinations thereof.

In a preferred embodiment, the crosslinks are selected from the group comprising hydroxylysylpyridinoline crosslinks, lysylpyridinoline crosslinks, pyridinium crosslinks, 3-hydroxypyridinium crosslinks and combinations thereof.

In a further embodiment, the protease-resistant fragments of type II collagen and/or type I collagen comprise from 2 to 15 amino acid residues, more particularly from 3 to 10 amino acid residues, preferably from 4 to 8 amino acid residues.

Preferably, the protease-resistant fragments of type II collagen and/or type I collagen are N-terminal and/or C-terminal collagen fragments.

To facilitate an immunological discriminability (low cross-reactivity) and thus an interference-free detection of the protease-resistant collagen fragments, it is preferred when the protease-resistant fragments of type II collagen are C-terminal collagen fragments and the protease-resistant fragments of type I collagen are N-terminal collagen fragments, or vice versa.

In a particularly preferred embodiment, the protease-resistant fragments of type II collagen are C-terminal and preferably crosslinked telopeptides, i.e., so-called C-terminal and preferably crosslinked type II collagen telopeptides (CTX-II), or fragments thereof, i.e., C-terminal and preferably crosslinked type II collagen telopeptide fragments (CTX-II fragments). The C-terminal telopeptides/telopeptide fragments can comprise in particular the amino acid sequence EKGPDP or an amino acid sequence according to SEQ ID NO: 1 as per the accompanying sequence listing. With regard to the possible crosslinks, reference is made to the statements so far.

In a further preferred embodiment, the protease-resistant fragments of type I collagen are N-terminal and preferably crosslinked telopeptides, i.e., so-called N-terminal and preferably crosslinked type I collagen telopeptides (NTX-I) or fragments thereof, i.e., N-terminal and preferably crosslinked type I collagen telopeptide fragments (NTX-I fragments). The N-terminal telopeptides/telopeptide fragments can comprise in particular the amino acid sequence TGVEGPKGDT (UniProtKB/Swiss-Prot: P02452.5) or an amino acid sequence according to SEQ ID NO: 2 as per the accompanying sequence listing. With regard to the possible crosslinks, reference is similarly made to the statements so far.

The composition and structure of the C-terminal and N-terminal telopeptides or telopeptide fragments that are mentioned in the two previous paragraphs are known per se to a person skilled in the art. By way of example, reference is made to the following references: Poole A R. "Immunochemical markers of joint inflammation, skeleton damage and repair: where are we now?" (Ann Rheum Dis. 1994 January; 53(1): 3-5); Garnero P, Piperno M, Gineyts E, Christgau S, Delmas P D, Vignon E. "Cross sectional evaluation of biochemical markers of bone, cartilage, and synovial tissue metabolism in patients with knee osteoarthritis: relations with disease activity and joint damage" (Ann Rheum Dis. 2001 June; 60(6): 619-26); Herrmann M, Seibel M J. "The amino- and carboxyterminal cross-linked telopeptides of collagen type I, NTX-I and CTX-I" (a comparative review. Clin Chim Acta. 2008 Jul. 17; 292(2): 57-75); Christgaue et al. Bone 2001; Garnero et al. "Association of baseline levels of markers of bone and cartilage degradation are associated with long-term progression of joint damage in patients with early rheumatoid arthritis: the Cobra study" (Arthritis Rheum. 2002a 46(11): 2847-56); Garnero et al. "Uncoupling of type II collagen synthesis and degradation predicts progression of joint damage in patients with knee osteoarthritis" (Arthritis Rheum. 2002b 46(10): 2613-24); Christgau et al. "Collagen type II C-telopeptide fragments as an index of cartilage degradation" (Bone 2001; 29: 209-215) doi: 10.1016/j.cca.2008.03.020 Epub 2008 Mar. 27 and Review. Erratum in: Clin Chim Acta. 2008 November; 397(1-2): 103. The content of the above-listed references is, with regard to the C-terminal and N-terminal telopeptides or telopeptide fragments described therein, incorporated in the present description by express reference.

In a preferred embodiment, step b) of the method according to the invention comprises a quantitative detection of the protease-resistant fragments of type II collagen and/or type I collagen, i.e., a determination of the amount of said collagen fragments that is present in the tissue sample.

Preferably, the degree of purity of the tissue sample with regard to cartilage tissue present therein is ascertained by means of the percentage shares of protease-resistant fragments of type II collagen and/or type I collagen.

In a further embodiment, step b) is carried out by contacting the protease-treated tissue sample with an antibody or antibody fragment, the antibody or the antibody fragment being specifically directed against protease-resistant fragments of type II collagen. This makes it possible to detect, more particularly quantitatively detect, such collagen fragments in the tissue sample, which is preferably in liquefied form.

In a further embodiment, step b) is carried out by contacting the protease-treated tissue sample with an antibody or antibody fragment, the antibody or the antibody fragment being specifically directed against protease-resistant fragments of type I collagen. This makes it possible to detect, more particularly quantitatively detect, such collagen fragments in the tissue sample, which is preferably in liquefied form.

The antibodies or antibody fragments that are used can be monoclonal or polyclonal. Such antibodies are prepared in accordance with standard methods which are known per se to a person skilled in the art and are described in particular by Harlow and Lane 1988 and Kohler and Milstein 1975 in "Continuous cultures of fused cells secreting antibody of predefined specificity" (Nature 1975, 256(5517): 495-7) and by Campbell, A. M. Laboratory Techniques in Biochemistry and Molecular Biology, volume 13 (1986).

In a further embodiment, an immunological technique is used to detect, more particularly quantitatively detect, binding of the antibody or antibody fragment to the protease-resistant fragments of type II collagen and/or type I collagen. The immunological technique is preferably selected from the group comprising ELISA techniques, immunoenzymatic techniques, immunofluorescence techniques, radioimmunology techniques, chemoimmunology techniques and proteome-analysis techniques. The techniques here are techniques which are sufficiently established in medicine and are validated, especially also CE-certified.

The use of an ELISA (Enzyme-Linked Immunosorbent Assay, Engvall, E. Meth Enzymol., 70, (1981)) is particularly preferred according to the invention. Firstly, ELISA has the advantage that it is a simple method to carry out in the laboratory. Secondly, it is advantageous that the detection limit achievable by means of ELISA is distinctly below the sensitivity required to carry out the method according to the invention. For example, it is possible to use the method according to the invention to process 100 mg of tissue, corresponding to a typical sample amount, in a 14 ml digest solution. Since cartilage contains about 25% of the wet weight in collagen, this means about 25 mg of collagen degradation products. From this, the protease-resistant fragments of type II collagen and/or type I collagen, more particularly the above-mentioned telopeptides CTX-II or NTX-I or the fragments thereof, make up about from 0.1 to 1% of this amount, i.e., about from 25 to 250 mg. Diluted in 14 ml, this is thus approximately from 2 to 20 µg/ml. However, the detection limits of an ELISA are typically within the lower to middle nanogram/milliliter range. This gives rise to a detection accuracy which is from 100 to 1000-fold above the required technical limit.

In a second aspect, the invention provides a method for preparing a cartilage cell culture. The method comprises the following steps:
 a) treating a cartilage tissue sample with a protease,
 b) testing the protease-treated cartilage tissue sample for the presence of protease-resistant fragments of type II collagen and/or type I collagen and
 c) culturing cartilage cells present in the tested cartilage tissue sample.

In a preferred embodiment, the cartilage tissue sample is a cartilage biopsy.

More particularly, the cartilage tissue sample can originate from a joint biopsy, preferably knee joint biopsy.

In a further embodiment, the cartilage tissue sample is cleaned mechanically, more particularly with the aid of a scalpel, before step a) is carried out.

In a further embodiment, connective tissue (such as synovia for example), superficial cartilage tissue, mineralized cartilage tissue and/or bone tissue, more particularly subchondral bone tissue, are removed from the cartilage tissue sample before step a) is carried out. Such a cleaning operation may be especially advantageous when the cartilage tissue sample originates from a cartilage/bone core biopsy.

In a further embodiment, the cartilage tissue sample is treated with the protease over a period of from h to 24 h, more particularly from 14 h to 24 h, preferably from 19 h to 24 h.

In a preferred embodiment, step b) comprises a quantitative detection of the protease-resistant fragments of type II collagen and/or type I collagen, i.e., a determination of the amount of said collagen fragments that is present in the cartilage tissue sample.

Preferably, the degree of purity of the cartilage tissue is ascertained by means of the percentage shares of protease-resistant fragments of type II collagen and/or type I collagen.

In a further embodiment, step b) is carried out by contacting the protease-treated cartilage tissue sample with an antibody or antibody fragment, the antibody or the antibody fragment being specifically directed against protease-resistant fragments of type II collagen. This makes it possible to detect, more particularly quantitatively detect, such collagen fragments in the cartilage tissue sample.

In a further embodiment, step b) is carried out by contacting the protease-treated cartilage tissue sample with an antibody or an antibody fragment, the antibody or the antibody fragment being specifically directed against protease-resistant fragments of type I collagen. This makes it possible to detect, more particularly quantitatively detect, such collagen fragments in the cartilage tissue sample.

An initial culturing of the cartilage cells preferably takes place in a so-called suspension culture. A suspension culture is a cell culture containing nonadherent cells. The cells remain in suspension, since they do not require direct contact to a substrate.

Preferably, the cartilage cells are cultured over a period of from 1 to 3 days, more particularly of 2 days.

A treatment of the cartilage tissue sample with protease in combination with a preferably multiday, more particularly two-day, suspension culture is especially advantageous, since it has emerged that neither bone cells nor endothelial cells survive such a cell-culture establishment phase.

In a further embodiment, step c) is carried out by using a so-called expansion medium. An expansion medium is understood to mean a cell culture medium used for cell propagation. The advantage of using such an expansion medium is that the proliferation rate of cleaned fibroblasts and osteoblasts is not higher than that of the cartilage cells and that cleaned endothelial cells also die in such a proliferation medium.

With regard to further features and advantages of the method, more particularly of the protease-resistant fragments of type II collagen and/or type I collagen, of the antibodies and of suitable immunological techniques for carrying out step b), full reference is made to the statements made in the context of the first aspect of the invention.

In a third aspect, the invention provides a method for preparing a cartilage cell-loaded implant, more particularly for use in matrix-assisted chondrocyte transplantation (MACT), comprising the following steps:
a) treating a cartilage tissue sample with a protease,
b) testing the protease-treated cartilage tissue sample for the presence of protease-resistant fragments of type II collagen and/or type I collagen,
c) culturing cartilage cells present in the tested cartilage tissue sample and
d) loading an implant with the cultured cartilage cells.

Implants suitable for loading with cartilage cells are especially collagen-containing implants.

Preferably, step d) is carried out by using an implant which is made up of layers and is composed of a component in the form of a membrane and a component in the form of a sponge, the component in the form of a sponge preferably having pores which are in the form of columns and which are oriented especially perpendicularly or substantially perpendicularly to the component in the form of a membrane. Preferably, such pores can be formed by means of one-sided lyophilization. Preferably, the component in the form of a membrane is a pericardium membrane and the component in the form of a sponge is a collagen sponge. A corresponding implant is commercially sold by the applicant, for example under the name Novocart® Basic or Novocart® 3D. With regard to further features and advantages of such an implant, reference is additionally made to EP 1 824 420 B1, the disclosure content of which concerning the implant described therein for repairing a cartilage defect is hereby incorporated in the present description by express reference.

With regard to further features and advantages of the method, full reference is made to the statements made in the context of the aspects of the invention so far.

In a fourth aspect, the invention provides for the use of protease-resistant fragments of type II collagen and/or type I collagen for the in vitro detection of cartilage tissue and/or for the in vitro determination of the purity of cartilage tissue.

With regard to further features and advantages of the use, more particularly of the protease-resistant fragments of type II collagen and/or type I collagen, full reference is likewise made to the statements made in the context of the aspects of the invention so far.

In a fifth aspect, the invention provides for the use of a kit, preferably immunological kit, for carrying out a method described in the context of the aspects of the invention so far.

The kit comprises at least two components selected from the group comprising antibodies, antibody fragments, antibody/reporter enzyme conjugates, antibody fragment/reporter enzyme conjugates, enzyme substrates, more particularly color substrates (chromogens), microtiter plates, buffer solutions, detergents, protein stabilizers, preservatives and combinations thereof.

The reporter enzymes can be selected from the group comprising horseradish peroxidase, alkaline phosphatase and glucose oxidase. Dye substrates can be selected from the group comprising para-nitrophenyl phosphate and o-phenylenediamine.

The above-mentioned buffer solutions can already contain customary additives, such as, for example, detergents, protein stabilizers and/or preservatives.

With regard to further features and advantages, full reference is similarly made to the statements made in the context of the aspects of the invention so far.

Further features and advantages of the invention are revealed by the embodiments described below, on the basis of figures, and figure descriptions of an example. It is possible here for individual features of the invention to be realized alone or in combination with one another. The described embodiments serve merely to elucidate and to provide a better understanding of the invention and are not to be understood in any way to be limiting.

DETAILED DESCRIPTION

Description of Experiments

1. The starting materials used for the digests were removed bone segments and cleaned cartilage segments from cartilage/bone cores from human patients. Pure synovial tissue, likewise from human patients, was also used. All tissues were processed in the same manner and used in wet weight according to the cartilage samples.

2. Recovery Experiment A

Figure 2:
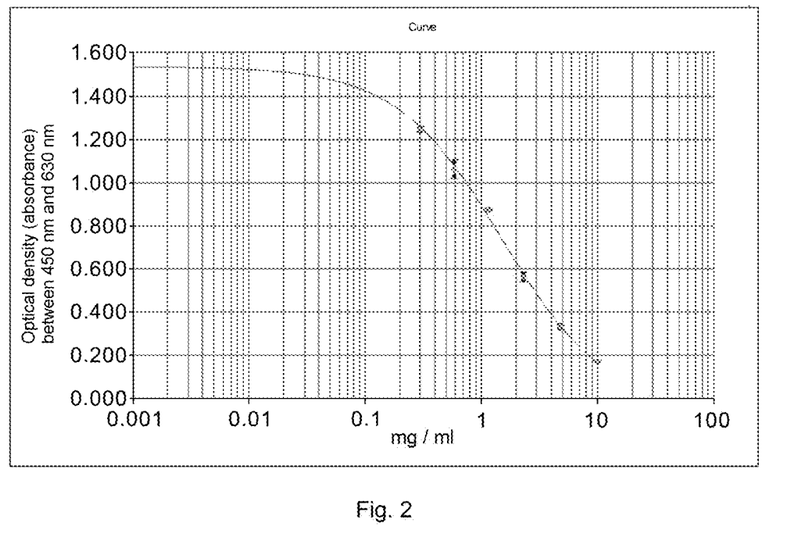
FIG. 2 shows schematically the standard curve of an ELISA (Urine CartiLaps® ELISA) used for the detection of CTX-II. Plotted on the y-axis is the optical density (absorbance) within a wavelength range of from 450 nm to 630 nm. Plotted on the x-axis is the concentration in mg/ml.
Figure 3:
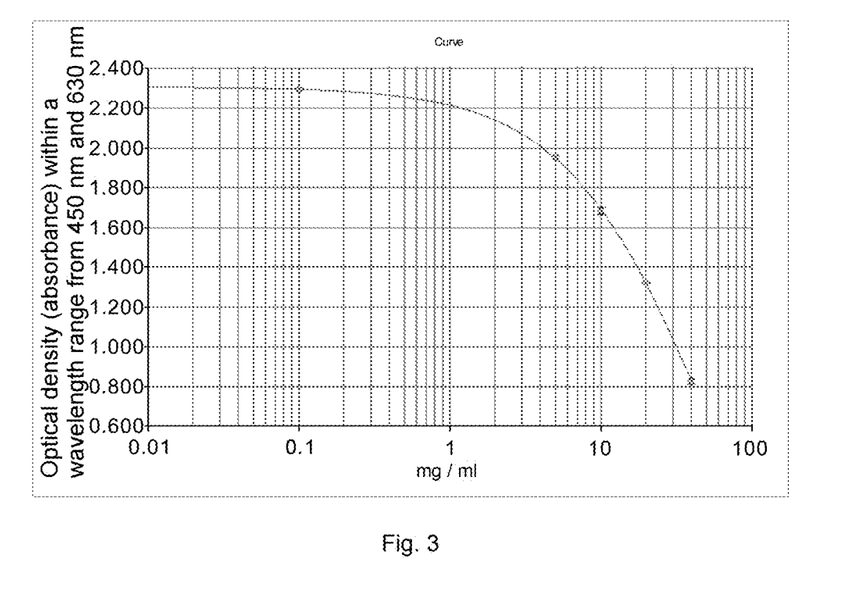
FIG. 3 shows schematically a standard curve of an ELISA (OSTEOMARK® NTX-Serum ELISA) used for the detection of NTX-I. Plotted on the y-axis is the optical density (absorbance) within a wavelength range of from 450 nm to 630 nm. Plotted on the x-axis is the concentration in nM BCE (Bone Collagen Equivalents).
Figure 4:
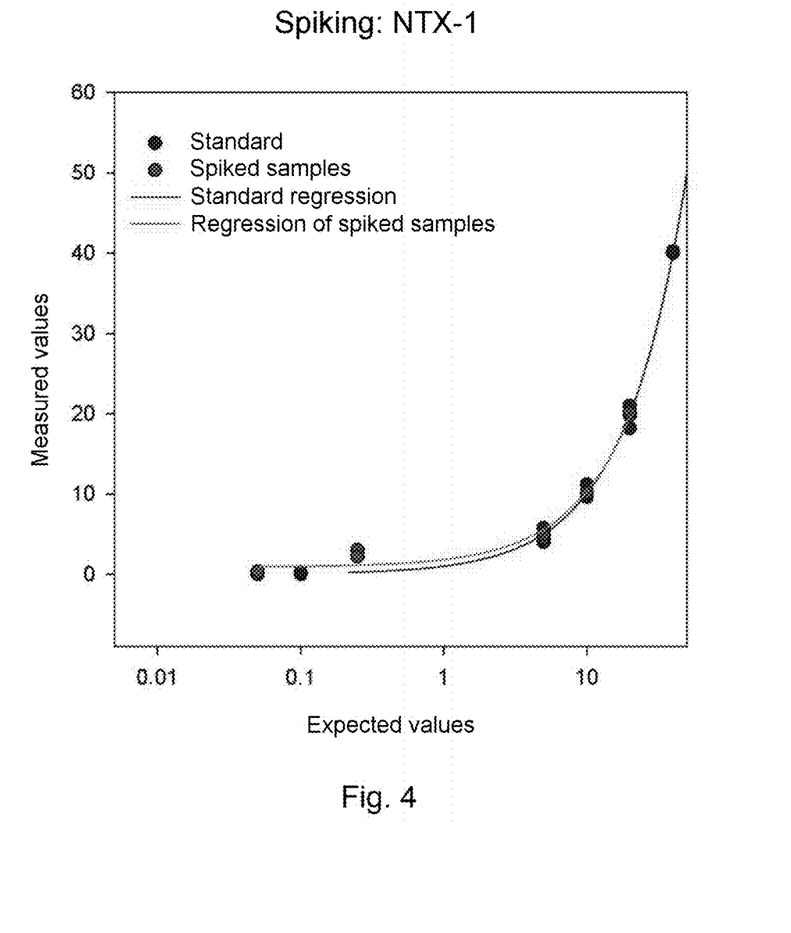
FIG. 4 shows schematically a logarithmic representation of the regular standard curve in buffer and of the standard curve in the presence of digest solution for NTX-I (1:50 cartilage digest). Indicated on the y-axis is the measured concentration in nM BCE/mm. Indicated on the x-axis is the expected concentration in nM BCE/mm. The logarithmic representation was selected so as to be able to appropriately depict the small concentrations.
Figure 5:
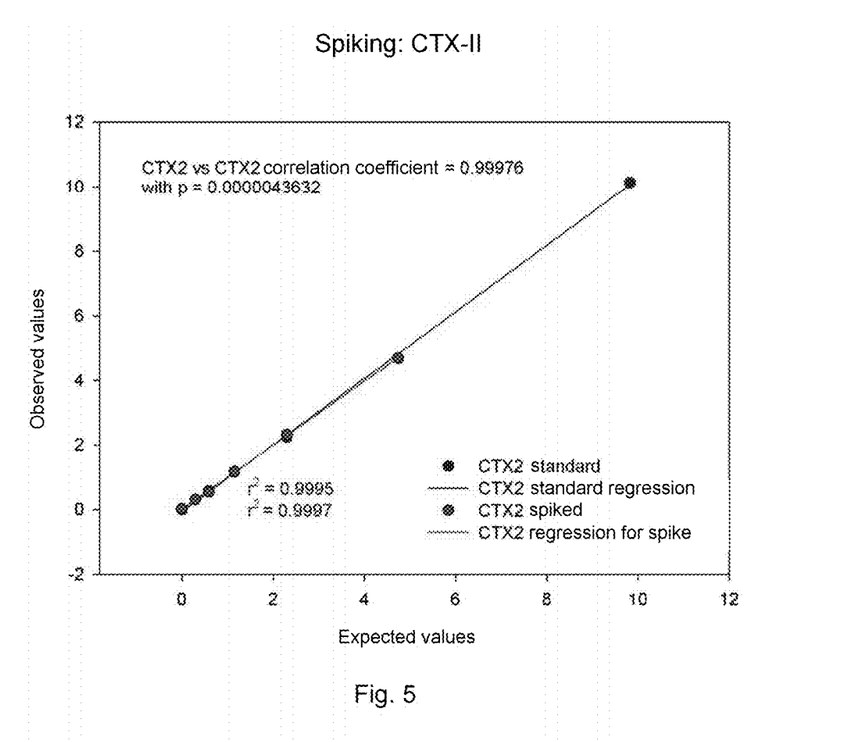
FIG. 5 shows schematically the representation of the regular standard curve in buffer and of the standard curve in the presence of digest solution for CTX-II (1:1000 synovial digest). Indicated on the y-axis is the measured concentration in ng/ml. Indicated on the x-axis is the expected concentration in ng/ml.

This recovery was carried out with the aid of the standards. This involved using the standards diluted 1:1 in the digest solution of the foreign tissue ("heterologous" digest solution): CTX-II in synovial digest, NTX-I in cartilage digest. The intention was to show that the presence of the foreign tissue digest does not cause quenching of the assays. FIG. 2 demonstrates that quenching or false-positive values did not arise in this experiment.

3. Recovery Experiment B

This variant investigated how well a defined amount of standard can be recovered in a homologous digest solution. This involved diluting the digest solution such that its original content of CTX-II or NTX-I could be measured and, as parallel sample in each case, a sample spiked with 40 nM BCE or 2.17 ng/ml CTX-II standard was also measured. The recovery rate was then calculated in percent. The statistics in relation thereto are as follows: the thus determined recovery rate for CTX-II was 90.1±1.4, and that for NTX-I was 100.9±15.2%; see Table 1 below:

TABLE 1

| Statistics relating to the spiking data | | | | | | |
|---|---|---|---|---|---|---|
| Spiking data | Size | Mean | Standard deviation | Standard deviation | C.I. of the mean | C.I. of the mean |
| Recovery of spiked NTX-I (%) | 12 | 100.87887 | 15.20866 | 4.39036 | 9.66312 | |
| Spiking data | Range | Maximum | Minimum | Median | 25% | 75% |
| Recovery of spiked NTX-I (%) | 56.38811 | 128.19811 | 71.81000 | 102.24872 | 89.47781 | 112.01241 |
| Spiking data | Size | Mean | Standard deviation | Standard deviation | C.I. of the mean | C.I. of the mean |
| Recovery of spiked CTX-II (%) | 16 | 8 | 90.09325 | 3.96857 | 1.40310 | 3.31781 |

TABLE 1-continued

| Statistics relating to the spiking data | | | | | | |
|---|---|---|---|---|---|---|
| Spiking data | Range | Maximum | Minimum | Median | 25% | 75% |
| Recovery of spiked CTX-II (%) | 12.22876 | 95.82523 | 83.59647 | 89.49629 | 87.80191 | 94.04336 |

4. Characterization of the Digest Solutions

Figure 6:
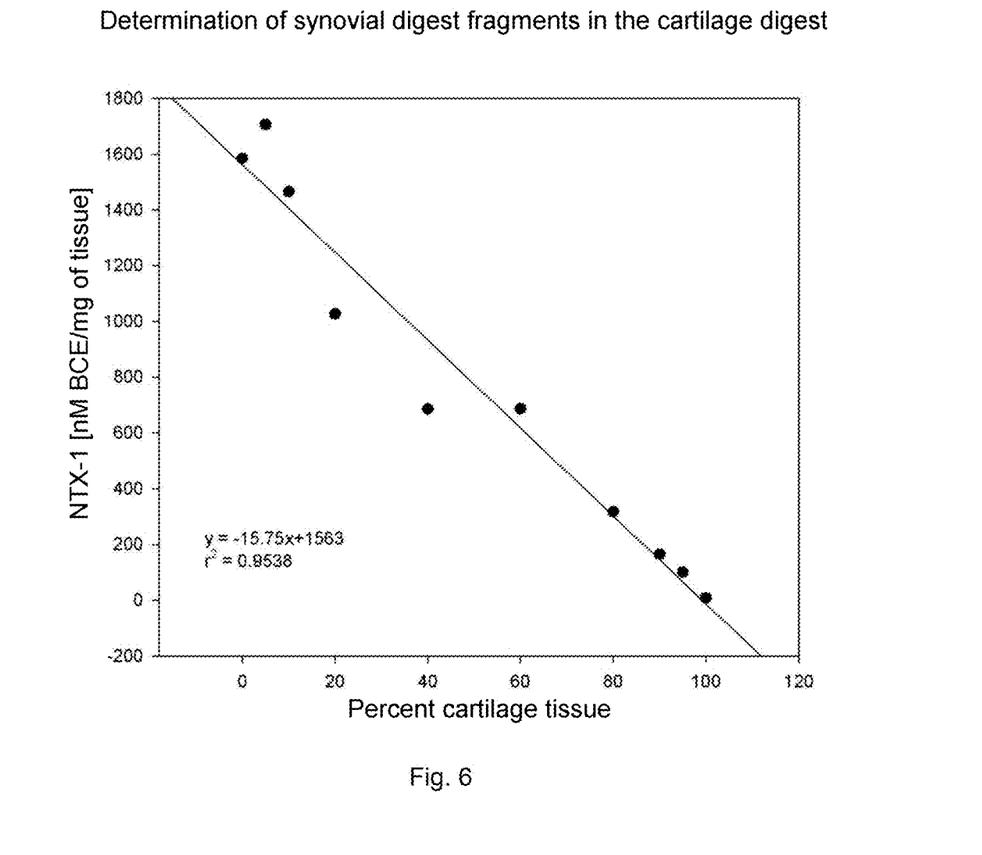
FIG. 6 shows schematically the result of the determination of synovial digest fragments in the cartilage digest. In this connection, "0% cartilage digest" means pure synovial digest. Indicated on the y-axis is the concentration of NTX-I in nM BCE/mg of tissue. Indicated on the x-axis is the proportion of cartilage digest in %.

The accuracy of detection of synovial fragments in the cartilage digest was determined. The above-described recovery experiments were carried out using the standards included in the assay kits. The advantage is a high precision; the disadvantage that the collagenase digest during production does not necessarily generate exactly the same antigen structures. Therefore, as a further validation step, cartilage digest was mixed with increasing proportions of synovial digest and the measurable proportion of NTX-I was determined in each case. The result is depicted in FIG. 6. In said figure, the regression line intersects the x-axis at about 0.6% of the maximum value of the pure synovial digest. The regression coefficient is 0.977 ($r^2$=0.9538). This yields an error of determination of below 3%, it clearly being 0.6% in this case.

Figure 7:
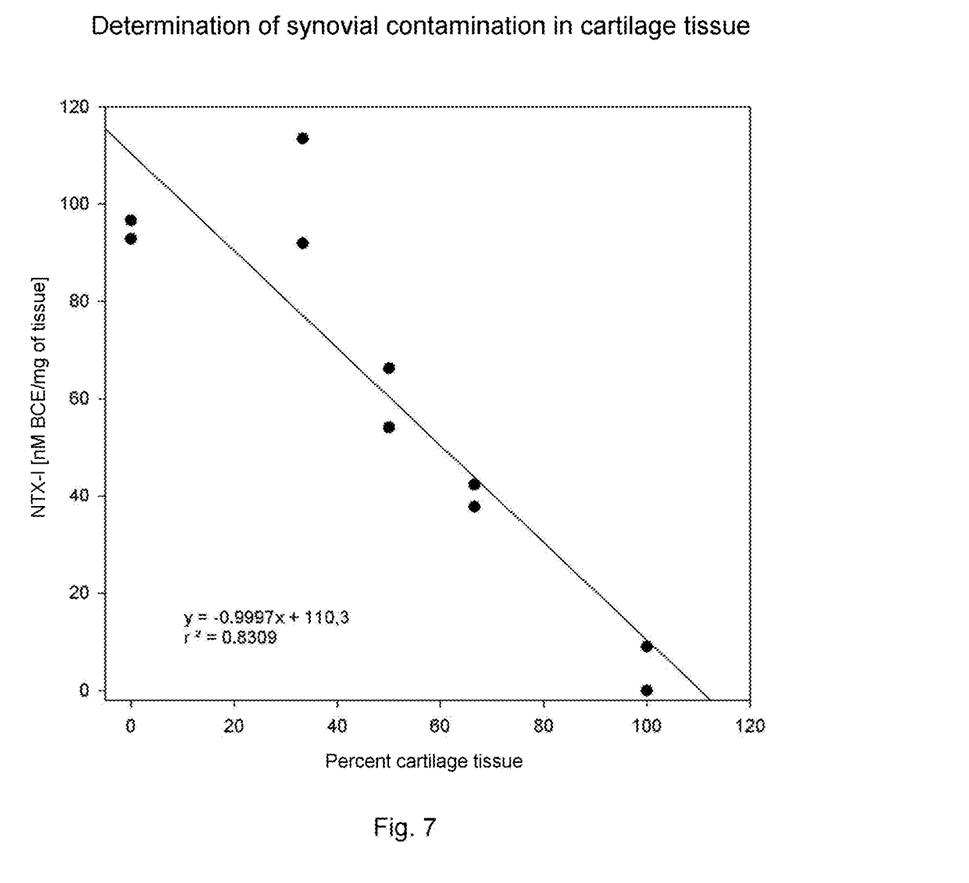
FIG. 7 shows graphically the result of a contamination experiment in which cartilage tissue was mixed with synovial tissue. The actual amounts weighed are: 100% synovia—115.7 mg cartilage, 66.6% synovia—67.9 mg+31.2 mg cartilage, 50% synovia—52.2 mg+53.6 mg cartilage and 33.3% synovia—30.4 mg+66.8 mg cartilage. The y-axis depicts the concentration of NTX-I in nM BCE/mg of tissue. The x-axis depicts cartilage tissue in %.

In the next stage, digests were not mixed; instead, fresh tissue from cartilage and synovia were digested together (see FIG. 7). However, this procedure was associated with some problems in terms of measurement. For instance, the piece of tissue had to be cleared of the excess buffer to determine the wet weight. Moreover, the one balance had to be effected in a sterile manner in order to prevent a contamination of the digest solution. As a consequence of these measures, the weighing precision was distinctly restricted and the resulting qualitative analysis impaired. Nevertheless, this method made it possible to generate a rough estimate for determining the detection limit of a synovial contamination.

Figure 8:
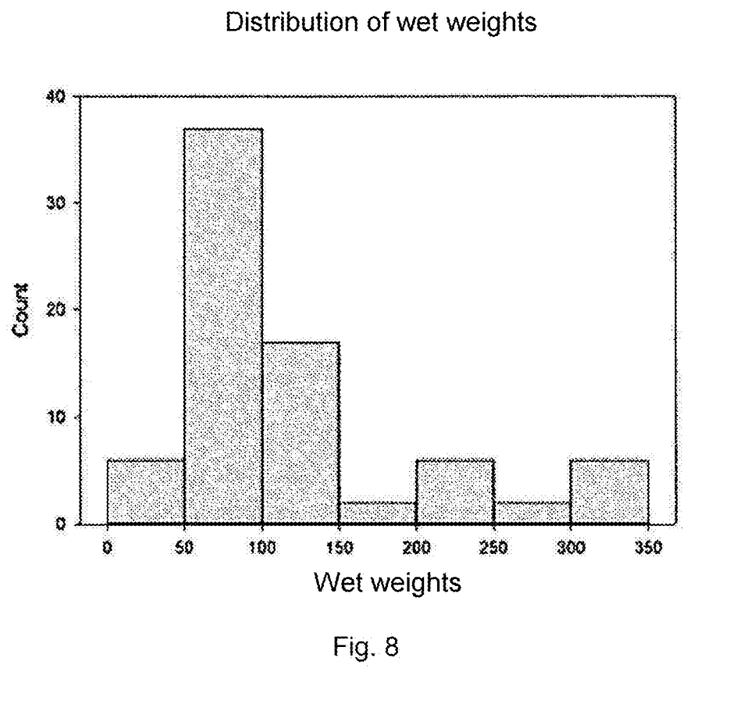
FIG. 8 shows a histogram in relation to the weight distribution of the measured samples composed of cartilage, synovia and bone.

The following statistics present the measured results from a series of tissue digests. In this connection, each cell is a multiple measurement of each donor tissue, with the multiple measurements of different individuals being performed on two different balances. The measured results of CTX-II in synovia and bone and the measured results of NTX-I in cartilage are not depicted, since they always remain below the detection limit of the particular ELISA. What were measured were absolute tissue amounts of altogether 76 samples within the range from about 20 mg to 320 mg (see FIG. 8), with the digest being carried out in 14 ml in each case (in line with the SAA). The data are depicted in Table 2 below.

TABLE 2

| Statistics for the crosslink determination in the tissue digests | | | | | | |
|---|---|---|---|---|---|---|
| Spiking data | Size | Missing | Mean | Standard deviation | Standard deviation | C.I. of the mean |
| Cartilage: CTX-II/mg | 5 | 0 | 379.59929 | 66.50570 | 29.74225 | 82.57773 |
| Cartilage: CTX-II/mg | 6 | 0 | 369.42578 | 140.50912 | 57.36261 | 147.45527 |
| Synovia: NTX-I/mg | 5 | 0 | 89.71775 | 40.76337 | 18.22993 | 50.61441 |
| Synovia: NTX-I/mg | 5 | 0 | 63.03821 | 9.99895 | 4.47167 | 12.41534 |
| Bone: NTX-I/mg | 2 | 0 | 20.49824 | 1.89793 | 1.34204 | 17.05225 |
| Bone: NTX-I/mg | 2 | 0 | 26.36596 | 2.46503 | 1.74304 | 22.14740 |
| Spiking data | Range | Maximum | Minimum | Median | 25% | 75% |
| Cartilage: CTX-II/mg | 185.63479 | 479.74332 | 294.10853 | 372.53333 | 329.08527 | 433.64628 |
| Cartilage: CTX-II/mg | 396.62359 | 557.43614 | 160.81256 | 395.79715 | 237.48199 | 472.11394 |
| Synovia: NTX-I/mg | 93.13859 | 140.55245 | 47.41386 | 102.03846 | 47.92717 | 125.34797 |
| Synovia: NTX-I/mg | 26.12503 | 80.02303 | 53.89800 | 61.08371 | 56.07894 | 70.97473 |
| Bone: NTX-I/mg | 2.68408 | 21.84028 | 19.15620 | 20.49824 | 19.15620 | 21.84028 |
| Bone: NTX-I/mg | 3.48608 | 28.10900 | 24.62292 | 26.36596 | 24.62292 | 28.10900 |

Units: CTX-II: ng/ml;
NTX-I: nM Bone Collagen Equivalents

Overall, the above yielded for type II collagen a detection limit for a sample which is used undiluted and for which at least 25 μg of cartilage tissue are required, and for type I collagen, 200 μg of synovial tissue or 1 mg of bone tissue. Since approximately 100 mg of wet weight were available as mean starting amount of processed material, this means that it was always possible to establish the identity of the cartilage tissue. The estimable limit of detectability of contamination with foreign tissue is 0.2% for synovial tissue and about 1% in the case of bone. In the case of relatively large primary weighed amounts, accuracy rises accordingly, since the measurable concentration in the digest solution rises up to 3-fold (because of weighed amount up to 300 mg). Conversely, detection accuracy falls accordingly when there are only small tissue amounts for processing in the 14 ml digest solution. For the purposes of illustration: based on the cartilage in FIG. 1, this means: said cartilage was in real life about mm in height, i.e., with a 4 mm cross section (the thickness of the trephine) and a 4 mm height (recognizable standard), had a volume of 48 mm$^3$, i.e., 48 mg. In the case of this weighed amount, the detection limit for synovia would be 400 µg, and this would be approximately 0.8%. Converted to height, this would be less than a height of 40 µm, i.e., a fraction of the height of the superficial layer. A height of 40 µm corresponds approximately to the height of the layer of covering cells. Based on bone, this would be a bone layer of about 200 µm in height.

5. Determination of the Concentrations of CTX-II in Various Mixtures of a Cartilage Digest and Synovial Digest A cartilage digest (production sample) was admixed with rising volumes of a synovial digest. According to the preliminary experiments, the samples had to be measured diluted differently, so that they were within the range of the standard (1:100 to 1:3000 dilutions). Furthermore, the sample dilutions had to be done in PBS, since only 3 mm Standard 07 (solvent) were supplied by the manufacturer. To improve the accuracy of measurement, the samples were measured in duplicate. Moreover, the pure tissue digests were prediluted, so as not to have to pipette small volumes less than 20 µl.

The concentrations of CTX-II were determined using the ELISA kit Urine CartiLaps® EIA (immunodiagnosticsystems) and the associated manufacturer's protocol.

In general, the incubation steps were carried out at 20° C. in a Thermomixer including an attachment for temperature adjustment of microtiter plates (Eppendorf).

Firstly, the kit components were brought to room temperature. The digest samples were thawed and they were admixed and shaken with 5 mM EDTA (0.5 M EDTA, diluted 1:100). Afterwards, the samples were left to sediment at room temperature for 30 minutes. Thereafter, the sample dilutions and also a mixture of standard stock solution and assay buffer were prepared. Using a multichannel precision pipette, 100 µl of a PBS-buffered solution containing biotinylated, synthetic peptide (CartiLaps antigen) were then added to the microwells of an ELISA plate precoated with streptavidin (12×8 microwells). After that, the ELISA plate was covered with adhesive tape and incubated at 20° C. for 30 minutes (statistically).

A wash buffer was prepared (10 ml of wash buffer concentrate (50×)+490 ml of distilled water). The ELISA plate was washed 5 times with 250 µl of wash buffer. Afterwards, 40 µl of standards, controls and samples were pipetted into the microwells of the ELISA plate. Thereafter, 100 µl of a TRIS-buffered solution containing a ready-to-use monoclonal antibody (primary antibody) were added to each microwell of the ELISA plate using a multichannel precision pipette. The ELISA plate was then covered with adhesive tape once again and incubated at from 4 to 8° C. for 21±3 hours (statistically). After that, the ELISA plate was rewashed 5 times with 250 µl of wash buffer. This was followed by adding 100 µl of a solution containing a peroxidase-conjugated antibody to each microwell of the ELISA plate using a multichannel precision pipette.

Afterwards, the ELISA plate was re-covered with adhesive tape and incubated at 20° C. for 60 minutes (statistically). Thereafter, the ELISA plate was washed again 5 times with 250 µl of wash buffer. Using a multichannel precision pipette, 100 µl of a chromogenic solution (tetramethylbenzidine (TMB) as substrate) were then added to each microwell of the ELISA plate.

Thereafter, the ELISA plate was re-covered with adhesive tape and incubated in the dark at 20° C. for 15 minutes (statistically). Finally, 100 µl of a stop solution (ready-to-use 0.18 mol/l sulfuric acid) were added to each microwell of the ELISA plate using a multichannel precision pipette.

Absorption was measured within a range from 450 nm to 630 nm (plate reader: ELX 808 from BioTek (R 530)) within 2 hours.

The 4P fitting of the series of CTX-II standards was evaluated using the software Gen5 1.01 from BioTek. The CTX-II concentrations of the controls and of the samples were calculated.

The following results were achieved:

Standard: good

Absolute abs. height is comparable with the data from the manufacturer's protocol for Urine CartiLaps® EIA. The $R^2$ of the fitting is good (0.999). The standards showed a regeneration (recovery) between 91 and 104%. The CVs were between 1 to 6%. One standard had a CV (variance) of 14%.

Controls: good

Both control samples were within the manufacturer's range and showed good CVs.

Contamination experiment digest samples: good

Figure 9:
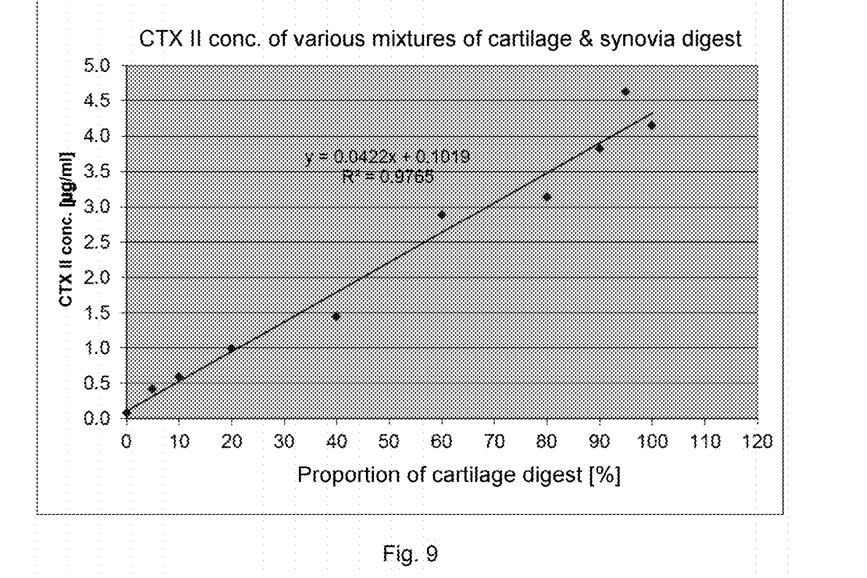
FIG. 9 shows graphically the concentrations of CTX-II in various mixtures of a cartilage digest and synovial digest. Indicated on the y-axis is the concentration of CTX-II in [μg/ml]. Indicated on the x-axis is the proportion of cartilage digest in [%].

The decreasing proportion by volume of the cartilage digest and the simultaneously increasing proportion by volume of the synovial digest could be clearly depicted (see FIG. 9). As a result of the measures taken, the gradations were additionally clearly identified.

6. Determination of the concentrations of NTX-I in various mixtures of a cartilage digest and synovial digest A synovial digest was admixed with rising volumes of a cartilage digest (production sample). According to the preliminary experiments, the samples had to be measured diluted differently, so that they were within the range of the standard (1:100 to 1:3 dilutions). A final 1:5 dilution of the standard and of the samples is obligatory. The samples were measured as a single value.

The samples of a BS study (sera) were measured undiluted in duplicate. A final 1:5 dilution of the standard and of the samples is obligatory.

The NTX-I concentrations were determined using the kit OSTEOMARK® NTx Serum (Wampole Laboratories, USA; cat. No. 9021, lot No. 13050074) and the associated manufacturer's protocol.

Firstly, the kit components were brought to room temperature. The digest samples (V=500 µl) were admixed with 5 µl of 0.5 M EDTA (5 mM EDTA). The digest contamination samples were prepared and diluted.

Thereafter, diluted samples were prepared using a sample dilution medium (2.5/1.25 nM BCE). Afterwards, the standards, controls and samples were obligatorily diluted 1:5. After that, a purified monoclonal mouse antibody (against NTx) conjugated with horseradish peroxidase was diluted with the aid of an antibody conjugate diluent (12 µl of conjugate concentrate (100×, CONJ)+12 ml of conjugate dilution medium (CONJ DIL)). Afterwards, 100 μl of diluted standards, controls, samples and diluted samples were pipetted into the microwells of an ELISA plate (12×8 microwells). The ELISA plate had been coated with adsorbed, synthetic NTx antigen.

Afterwards, 100 μl of the diluted antibody conjugate solution (lx) were added to the microwells of the ELISA plate using a multichannel precision pipette. Thereafter, the ELISA plate was masked and mixed at 500 rpm for 20 seconds. Afterwards, the ELISA plate was incubated at 23° C. for 90 minutes (statistically). A wash buffer (15 ml of wash buffer concentrate (30×)+435 ml of distilled water, 5 minutes of mixing) was then prepared.

Thereafter, the chromogen reagent (tetramethylbenzidine) was diluted (200 μl of chromogen concentrate (100×)+20 ml of buffered substrate (hydrogen peroxide)). The ELISA plate was washed 5 times with 300 μl of wash buffer. After that, 200 μl of the chromogen solution (1×) were added to the microwells of the ELISA plate using a multichannel precision pipette. The ELISA plate was then remasked and incubated at 23° C. for 30 minutes (statistically). Afterwards, 100 μl of a stop solution (1 N sulfuric acid) were pipetted into each microwell of the ELISA plate, before the plate was incubated again at 23° C. for 5 min.

Thereafter, the absorbance values were determined using a microplate reader (ELX 808 from BioTek (R 530)) within a range from 450 nm to 630 nm.

The 4P fitting of the series of NTX-I standards was determined using the software Gen5 1.01 from BioTek. The NTX-I concentrations of the samples were calculated.

In this connection, the following results were obtained:
General criteria: good
Mean absorbance of the 0 standard (0 BCE): nominal: >1.3; actual: about 2.3
Absorbance range of the standard (0 and 40 nM BCE): nominal: >0.9; actual: about 1.5
Standard: good
Fitting is good ($R^2$=0.999), CVs<5%, regenerations (re-coveries) 98-102%
LLOQ:
The standard could not be extended downward.
Controls: decent
Both control samples were just below the manufacturer's range (4 or 7%), but still clearly within the confidence interval
Digest samples: good
The decreasing proportion by volume of the synovial digest and the simultaneously increasing proportion by volume of the cartilage digest (production sample) could be clearly depicted (see FIG. 6).
Serum samples: good
In 5 out of 5 samples measured undiluted, it was possible to measure NTX-I stably.
The CVs were between 1 to 9%. The NTX-I concentration was 14.4 nM BCE (±2.7) (range: 10.9 to 19.3)

The invention claimed is:

1. A method for the in vitro determination of the degree of purity of cartilage tissue, comprising the following steps:
   a) treating a tissue sample with a protease and
   b) testing the protease-treated tissue sample for the presence of protease-resistant fragments of type II collagen and type I collagen, wherein the degree of purity of the tissue sample with regard to cartilage tissue present therein is ascertained by calculating percentage of the protease-resistant fragments of type II collagen and type I collagen within the tissue sample wherein the tissue sample is a cartilage biopsy or a fragment thereof, wherein the protease-resistant fragments of type II collagen are C-terminal crosslinked type II collagen telopeptides (CTX-II) or fragments thereof and wherein the protease-resistant fragments of type I collagen are N-terminal crosslinked type I collagen telopeptides (NTX-I) or fragments thereof.

2. The method as claimed in claim 1, wherein the tissue sample is a joint biopsy.

3. The method as claimed in claim 1, wherein superficial cartilage tissue, mineralized cartilage tissue and/or bone tissue is removed from the tissue sample before step a) is carried out.

4. The method as claimed in claim 1, wherein the protease is collagenase.

5. The method as claimed in claim 1, wherein the protease-resistant fragments of type II collagen and/or type I collagen have crosslinks selected from the group comprising allysine crosslinks, hydroxyallysine crosslinks, dehydrohydroxylysinonorleucine crosslinks, dehydrolysinonorleucine crosslinks, hydroxylysino-5-ketonorleucine crosslinks, dihydroxylysinonorleucine crosslinks, hi stidinohydroxylysinonorleucine crosslinks, hydroxylysylpyridinoline crosslinks, lysylpyridinoline crosslinks, pyridinium crosslinks, 3-hydroxypyridinium crosslinks, histidinohydroxymerodesmosine crosslinks and combinations thereof.

6. The method as claimed in claim 1, wherein step b) is carried out by contacting the protease-treated tissue sample with an antibody or antibody fragment, the antibody or the antibody fragment being specifically directed against protease-resistant fragments of type II collagen.

7. The method as claimed in claim 1, wherein step b) is carried out by contacting the protease-treated tissue sample with an antibody or antibody fragment, the antibody or the antibody fragment being specifically directed against protease-resistant fragments of type I collagen.

8. The method as claimed in claim 6, wherein an immunological technique is used to detect the binding of the antibody or antibody fragment to the protease-resistant fragments.

9. A method for preparing a cartilage cell culture, comprising the following steps:
  a) treating a cartilage tissue sample with a protease,
  b) testing the protease-treated cartilage tissue sample for the presence of protease-resistant fragments of type II collagen and type I collagen,
  c) identifying and isolating cartilage cells from the tested protease-treated cartilage tissue sample, and
  d) culturing cartilage cells present in the tested cartilage tissue sample, wherein in step c), the cartilage cells are identified by ascertaining the degree of purity of the cartilage tissue by calculating percentage of the protease-resistant fragments of type II collagen and type I collagen within the tissue sample, and wherein the protease-resistant fragments of type II collagen are C-terminal crosslinked type II collagen telopeptides (CTX-II) or fragments thereof and wherein the protease-resistant fragments of type I collagen are N-terminal crosslinked type I collagen telopeptides (NTX-I) or fragments thereof.

10. A method for preparing a cartilage cell-loaded implant comprising the following steps:
  a) treating a cartilage tissue sample with a protease,
  b) testing the protease-treated cartilage tissue sample for the presence of protease-resistant fragments of type II collagen and type I collagen,
  c) identifying and isolating cartilage cells from the tested protease-treated cartilage tissue sample,
  d) culturing cartilage cells present in the tested cartilage tissue sample and
  e) loading an implant with the cultured cartilage cells, wherein in step c), the cartilage cells are identified by ascertaining the degree of purity of the cartilage tissue by calculating percentage of the protease-resistant fragments of type II collagen and type I collagen within the tissue sample, and wherein the protease-resistant fragments of type II collagen are C-terminal crosslinked type II collagen telopeptides (CTX-II) or fragments thereof and wherein the protease-resistant fragments of type I collagen are N-terminal crosslinked type I collagen telopeptides (NTX-I) or fragments thereof.

* * * * *